United States Patent [19]  [11]  4,359,585
Campbell et al.  [45]  Nov. 16, 1982

[54] CATALYST PASSIVATION IN PRODUCTION OF AMINES

[75] Inventors: Charles R. Campbell, Pensacola, Fla.; Charles E. Cutchens, Decatur, Ala.

[73] Assignee: Monsanto Company, St. Louis, Mo.

[21] Appl. No.: 141,836

[22] Filed: Apr. 21, 1980

[51] Int. Cl.³ .............................................. C07C 85/12
[52] U.S. Cl. .................................... 564/492; 564/490; 564/498
[58] Field of Search ............................... 564/492, 490

[56] References Cited
U.S. PATENT DOCUMENTS 3,056,837  10/1962  Steeman .......................... 564/492 X
3,821,305  6/1974  Bartalini et al. .................... 564/492

Primary Examiner—Robert V. Hines
Attorney, Agent, or Firm—Thomas Y. Awalt, Jr.

[57] ABSTRACT

This is an improvement in a process for the production of an amine such as hexamethylenediamine from a nitrile such as adiponitrile where the nitrile is hydrogenated under pressure in the presence of a Raney nickel catalyst, the reaction being conducted in a reactor from which is discharged a product stream containing both the amine and the Raney nickel catalyst. The improvement comprises charging to the process discharge stream containing the product amine and the Raney nickel catalyst, an inorganic base, whereby the Raney nickel catalyst is passivated and catalytic decomposition of the amine is substantially decreased.

13 Claims, 1 Drawing Figure

U.S. Patent    Nov. 16, 1982    4,359,585
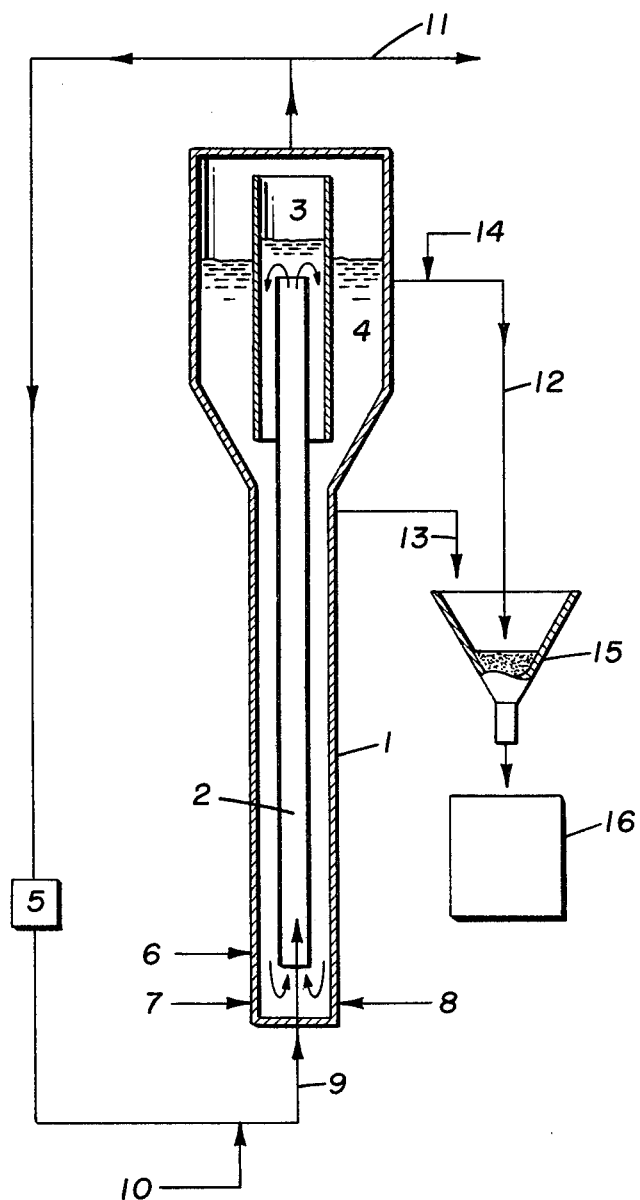

CATALYST PASSIVATION IN PRODUCTION OF AMINES

FIELD OF THE INVENTION

The invention relates to a process for the production of an amine such as hexamethylenediamine from a nitrile such as adiponitrile where the nitrile is hydrogenated under pressure in the presence of a Raney nickel catalyst, the reaction being conducted in a reactor from which is discharged a product stream containing both the amine and Raney nickel catalyst.

BACKGROUND OF THE INVENTION

It is well known that amines such as hexamethylene diamine can be produced by the catalytic hydrogenation of nitriles such as adiponitrile in the presence of Raney catalysts.

One such process is described in U.S. Pat. No. 3,821,305, in which hydrogenation is conducted in liquid phase at pressures of from 20–50 atmospheres and temperatures of 60°–100° C. in the presence of finely divided Raney catalyst and an inorganic base. Hydrogen and adiponitrile are fed into a liquid reaction medium consisting of hexamethylenediamine, water, the inorganic base, and the catalyst, in which medium the content of base is maintained in the range of 0.2–12 moles per kilogram of catalyst, while the content of water is maintained in the range of 2–130 moles per mole of the base.

The process discharge stream in the above described process contains both Raney catalyst and the product hexamethylenediamine, from which it is desirable to recover substantially pure hexamethylenediamine by distillation, and to recycle the Raney catalyst.

During such separation procedures, the crude amine is exposed to the Raney nickel catalyst under conditions favoring its decomposition or dehydrogenation. This decomposition is substantial if the catalyst is not separated or passivated immediately after the process discharge exits the reactor. Even the small amount of catalyst that normally gets through most commercial processes for removing catalyst (centrifuge, decantation, filtration) result in significant decomposition of amine if the catalyst is not passivated.

The substantial elimination of such decomposition would constitute a significant improvement in the art and is an object of this invention.

SUMMARY OF THE INVENTION

Briefly, the invention is an improvement in a process for the production of an amine such as hexamethylenediamine from a nitrile such as adiponitrile where the nitrile is hydrogenated under pressure in the presence of a Raney nickel catalyst continuously in a reactor thereby to produce an amine which is discharged in a stream from which is recovered both hexamethylenediamine and Raney nickel catalyst. The improvement comprises charging to the process discharge stream containing the product amine and the Raney nickel catalyst an inorganic base whereby the Raney nickel catalyst is passivated and catalytic decomposition of the amine is substantially decreased.

The inorganic base can be the hydroxide of any metal. Preferred for their passivation effect are the hydroxides of alkali metals.

DETAILED DESCRIPTION OF THE INVENTION

While the invention is applicable to any process for the production of an amine from a nitrile in which a Raney nickel catalyst is employed, the invention will be described in the context of a preferred process for such production.

The process for the production of the amine is preferably carried out in pressures of 20–50 atmospheres in temperatures of 60°–100° C., by feeding molecular hydrogen and adiponitrile into a liquid reaction medium containing, along with the hexamethylenediamine produced, water, sodium hydroxide and a finely divided Raney catalyst dispersed in the liquid components of the reaction medium. The catalyst, which may be Raney nickel, or Raney nickel containing small amounts of other metals such as chromium, loses all or most of its activity during hydrogenation. In order to maintain a given level of catalytic activity with the catalytic mass, it is necessary for the catalyst in the reaction medium to be gradually replaced. This replacement is effected by feeding fresh catalyst to the reaction vessel and removing a quantity of reaction medium which contains an amount of catalyst equal to that supplied. The fed catalyst may consist of a mixture of fresh catalyst and of recycled catalyst. Recycled catalyst is catalyst that has been washed prior to re-use.

The reaction medium preferably contains:

(1) a quantity of catalyst in excess of 1 part, by weight, per 100 parts of liquid reaction medium (hexamethylenediamine, water and sodium hydroxide), the upper limit depending solely on the fluidity of the reaction medium; the preferred range is from 3 to 35 parts per 100 parts by weight of the liquid reaction medium;

(2) a quantity of sodium hydroxide in the range of 0.2 to 12 moles per kilogram of catalyst and preferably between 1 and 3 moles per kilogram of catalyst;

(3) a quantity of water in the range of 2 to 130 moles per mole of sodium hydroxide and preferably between 7 and 70 moles per mole of sodium hydroxide.

Substantially similar results in the production of the amine can be obtained by using, instead of sodium hydroxide, a hydroxide of any other of the alkali metals. Throughout the following description, however, reference will be made to the preferred sodium hydroxide.

The liquid part of the reaction medium, under the starting conditions already specified, and within the preferred range of ratio of water to sodium hydroxide, consists of two phases. One phase, amounting to 0.5–5.0 parts per 100 parts of the other phase, consists of an aqueous solution of sodium hydroxide whose concentration is in the range of 25 to 55 percent by weight. The other phase consists of hexamethylendiamine containing water and small amounts of sodium hydroxide. The aqueous solution of sodium hydroxide, which is the heavier phase, contains most of the catalyst.

The equipment for continuous operation of the process is of conventional type. An example of this, which is not limitive of the invention, is shown in the accompanying drawing.

The equipment consists essentially of a vertical tubular reaction vessel, 1, provided inside with an injection device, 2, such as to promote the agitation of the reaction medium resulting from the hydrogen flow, and at the top with containers, 3 and 4, which enable the separation of the gas from the liquid and the drawing off from the reaction vessel of a hydrogenated product having a low content of catalyst thus making it possible to maintain in the reaction vessel relatively high concentrations of catlyast—for example, 10 and 20 parts of catalyst per 100 parts by weight of liquid reaction medium.

The equipment also includes a gas re-cycling pump, 5, and pipes for feeding the reaction vessel with adiponitrile solution of sodium hydroxide, 8, and hydrogen, 9. The hydrogen consumed is replaced by feeding fresh hydrogen through pipe 10.

Part of the gas is vented through pipe 11, the purpose of this release being to maintain the hydrogen content in the re-cycled gas above a given value.

Hexamethylenediamine is discharged through pipe 12.

Pipe 13 is used for removing an amount of reaction medium whose catalyst content is equivalent to the amount supplied through pipe 7. In this way, the concentration of catalyst in the reaction medium remains constant.

According to the present invention the inorganic base is introduced through pipe 14. The Raney nickel catalyst contained in the product discharge stream is collected at filter 15, and the relatively pure hexamethylenediamine is collected in container 16.

While the inorganic base is preferably added as close to the reactor discharge point as possible, it can, of course, be added at any point downstream from the reactor in order to passivate the catalyst.

Any amount of inorganic base added to the process discharge stream will cause some deactivation of the catalyst, and lessen, to a certain extent, the catalytic decomposition of hexamethylenediamine. At a level of 0.4 caustic/catalyst weight ratio, catalyst passivation is significant. At a caustic/catalyst weight ratio of 10, catalyst activity is essentially eliminated, and there is little, if any, decomposition of the hexamethylenediamine. A suitable weight ratio range is 0.4–1.1 and a preferred range is 0.6–0.9. Higher ratio ranges are effective but uneconomical.

It is important to note that most commercial processes for removing catalyst and purifying hexamethylenediamine are by centrifuge, decantation, and filtration. The addition of an inorganic base, besides pacifying the catalyst, also improves the settling properties of the catalyst and accordingly facilitates removal of the catalyst whether by centrifuge, decantation or filtration.

EXAMPLES

In each example, a reactor was charged with 70 grams hexamethylenediamine (HMD), and the amount shown of catalyst in an aqueous slurry. Sodium hydroxide was added so as to provide a weight ratio as shown. A nitrogen blanket was applied and the reactor held at 50° C. (isothermal) for two hours. The reaction mix was then refluxed at atmospheric pressure for five hours. A sample of the reaction mix was then analyzed. The initial charge and the results of analysis are shown at Table 1. In Examples 1–7, only new catalyst was employed. In Examples 8–11, the catalyst employed was collected from the crude HMD product obtained as described in the specification.

The data shows that the sodium hydroxide did not deactivate the catalyst because water washing returned the catalyst to an active state. After Example 12 was completed, the catalyst was recovered and water-washed several times to remove the sodium hydroxide. It was then used in Example 13 which shows an 8.3 weight % hexamethylenediamine decomposition.

TABLE 1

| | CHARGE, grams | | | NaOH/Cat. Ratio | WT % HMD Lost | WT % DECOMPOSITION PRODUCTS | | | | | |
|---|---|---|---|---|---|---|---|---|---|---|---|
| Ex. | HMD | NaOH | Catalyst | | | HMI | ACH | ACN | ADN | BHMT | UNKNOWNS |
| NEW CATALYST | | | | | | | | | | | |
| 1 | 70 | 0.75 | 0.5 | 1.5 | 0.5 | <0.01 | 0.45 | 0.04 | nil | nil | 0.02 |
| 2 | 70 | 0.39 | 0.5 | 0.78 | 1.9 | <0.01 | 1.2 | 0.22 | 0.09 | nil | 0.02 |
| 3 | 70 | 0.18 | 0.5 | 0.36 | 7.1 | 0.19 | 3.1 | 2.4 | 0.05 | 1.1 | 0.17 |
| 4 | 70 | 0 | 0.5 | — | 31 | 9.2 | 7.2 | 6.0 | 0.64 | 5.9 | 2.2 |
| 5 | 70 | 0.17 | 0.25 | 0.68 | 0.7 | <0.01 | 0.63 | 0.45 | 0.02 | 0.42 | 0.21 |
| 6 | 70 | 0.18 | 1.0 | 0.18 | 10.8 | 1.1 | 2.9 | 3.2 | 0.09 | 2.2 | 0.33 |
| 7 | 70 | 0 | 0.13 | — | 23 | 4.4 | 5.3 | 5.9 | 0.63 | 3.1 | 1.7 |
| CATALYST CARRIED-OVER IN LPD CRUDE PRODUCT | | | | | | | | | | | |
| 8 | 70 | 0 | 0.5 | — | 52 | 18.9 | 4.6 | 4.4 | 0.93 | 6.2 | 5.3 |
| 9 | 70 | 0.78 | 0.5 | 1.56 | 6.6 | 0.39 | 3.5 | 0.2 | 0.05 | 0.49 | 1.0 |
| 10 | 70 | 0.19 | 0.25 | 0.76 | 5.1 | 0.02 | 3.2 | 1.2 | 0.05 | 0.08 | 0.54 |
| 11 | 70 | 0.16 | 0.13 | 1.23 | 4.6 | 0.02 | 2.5 | 0.78 | 0.02 | nil | 0.36 |
| NEW CATALYST | | | | | | | | | | | |
| 12 | 70 | .75 | 0.5 | 1.5 | 2.1 | .03 | 1.2 | .15 | .02 | .19 | .52 |
| 13 | 70 | 0 | Catalyst rec. from Run #12 | — | 8.3 | .74 | 3.7 | .67 | .05 | 1.4 | .24 |

ACH = azacycloheptene-1
ADN = adiponitrile
HMI = hexamethyleneimine
HMD = hexamethylenediamine
BHMT = bis-hexamethylenetriamine

We claim:

1. In a process for the production of an amine from a nitrile where the nitrile is hydrogenated under pressure in the presence of a Raney nickel catalyst continuously in a reactor thereby to produce the amine which is discharged in a stream from which is recovered both the amine and Raney nickel catalyst, the improvement comprising charging to the process discharge stream comprising the product amine and Raney nickel catalyst an inorganic base whereby the Raney nickel catalyst is passivated and catalytic decomposition of the amine is substantially decreased.

2. The process improvement of claim 1 wherein the weight ratio of the inorganic base to the catalyst is about 0.4–1.1.

3. The process improvement of claim 1 wherein the weight ratio of the inorganic base to the catalyst is about 0.6–0.9.

4. The process improvement of claim 1 wherein the inorganic base is sodium hydroxide.

5. In a process for the production of hexamethylenediamine from adiponitrile where the adiponitrile is hydrogenated under pressure in the presence of a Raney nickel catalyst continuously in a reactor thereby to produce hexamethylenediamine which is discharge in a stream from which is recovered both hexamethylenediamine and Raney nickel catalyst, the improvement comprising charging an inorganic base to the process discharge stream containing the product hexamethylenediamine and Raney nickel catalyst whereby the Raney nickel catalyst is passivated and catalytic decomposition of the hexamethylenediamine is substantially decreased.

6. The process improvement of claim 5 wherein the weight ratio of the inorganic base to the catalyst is 0.4–1.1.

7. The process improvement of claim 5 wherein the weight ratio of the inorganic base to the catalyst is 0.6–0.9.

8. The process improvement of claim 5 wherein the inorganic base is sodium hydroxide.

9. The process improvement of claim 5 wherein the inorganic base is charged to the process discharge stream under hydrogen pressure.

10. A process for the passivation of Raney nickel catalyst in a process discharge stream comprising hexamethylenediamine and Raney nickel catalyst so as to prevent decomposition of the hexamethylenediamine and permit recovery of the catalyst, the process comprising charging under hydrogen pressure an inorganic base to the process discharge stream.

11. The process of claim 10 wherein the weight ratio of the inorganic base to the catalyst is 0.4–1.1.

12. The process of claim 10 wherein the weight ratio of the inorganic base to the catalyst is 0.6–0.9.

13. The process of claim 10 wherein the inorganic base is sodium hydroxide.

* * * * *